United States Patent [19]
Enggaard

[11] Patent Number: 6,076,390
[45] Date of Patent: Jun. 20, 2000

[54] METHOD FOR CALIBRATION OF AN ANALYSIS SYSTEM AND AN ANALYSIS SYSTEM

[75] Inventor: Chrstian Peter Enggaard, Hillerød, Denmark

[73] Assignee: Danfoss A/S, Nordborg, Denmark

[21] Appl. No.: 09/202,051

[22] PCT Filed: Jul. 2, 1997

[86] PCT No.: PCT/DK97/00288

§ 371 Date: Dec. 7, 1998

§ 102(e) Date: Dec. 7, 1998

[87] PCT Pub. No.: WO98/01741

PCT Pub. Date: Jan. 15, 1998

[30] Foreign Application Priority Data

Jul. 5, 1996 [DE] Germany .......................... 196 27 046

[51] Int. Cl.[7] .................................................. G01N 1/00
[52] U.S. Cl. ............................................................ 73/1.06
[58] Field of Search .................... 73/1.01, 1.02, 73/1.07, 863.23, 864.73, 864.34, 864.81, 61.59, 64.56, 1.06; 436/52, 178; 422/68.1

[56] References Cited

U.S. PATENT DOCUMENTS

| | | | |
|---|---|---|---|
| 4,410,211 | 10/1983 | Sugawara et al. | 73/863.23 |
| 4,942,135 | 7/1990 | Zaromb | 73/863.23 |
| 5,448,922 | 9/1995 | Kimbell et al. | 73/863.23 |

FOREIGN PATENT DOCUMENTS

WO 96/01989  1/1996  WIPO.

*Primary Examiner*—Robert Raevis
*Attorney, Agent, or Firm*—Lee, Mann, Smith, McWilliams, Sweeney & Ohlson

[57] ABSTRACT

The invention concerns a method for calibration of an analysis system (1) having a diaphragm (2), the outside of which is immersed into a medium (3) to be analyzed, and on the inside of which a carrier fluid (9) for the admission of a species penetrating the diaphragm (2) is flowing. On this system a calibration in situ should be possible, without causing high costs for constructional measures. For this purpose, the carrier fluid is, in a calibration step, retained on the inside of the diaphragm (2) for a predetermined sojourn time, and then the load of species in the carrier fluid (9) is determined. In a further calibration step, the carrier fluid is led past the diaphragm at a speed also used for measurements, and the load of species in the carrier fluid is measured. Then the penetration behavior of the diaphragm is determined on the basis of both load values.

8 Claims, 1 Drawing Sheet

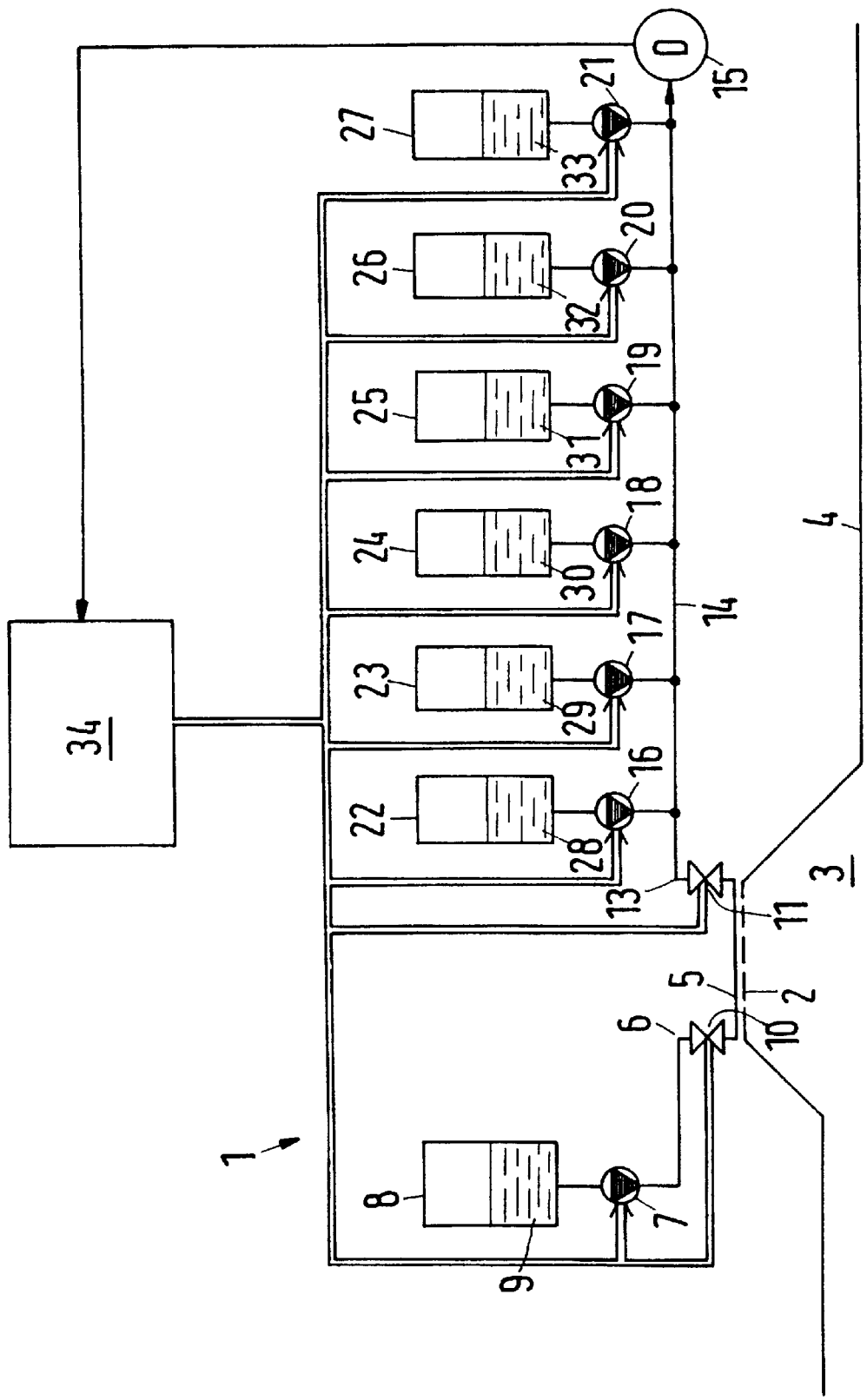

METHOD FOR CALIBRATION OF AN ANALYSIS SYSTEM AND AN ANALYSIS SYSTEM

The invention concerns a method for calibration of an analysis system having a diaphragm, the outside of which is immersed into a medium to be analysed, and on the inside of which a carrier fluid for the admission of a species penetrating the diaphragm is flowing.

Further, the invention concerns an analysis system with a diaphragm, the outside of which is immersed into a medium to be analysed, by which a flow path is arranged on the inside of the diaphragm, the inlet side of which is connected to a reservoir of a carrier fluid and the outlet side of which is connected to a detector.

Such analysis systems are working with some sort of dialysis, i.e. the species to be analysed penetrates the diaphragm and thus reaches the carrier fluid. This penetration occurs for instance as diffusion. The species can for instance consist of ions or other low-molecular parts, which are contained in the fluid to be analysed, which is bearing against the outside of the diaphragm or flows past it.

It is known that such analysis systems must be calibrated at certain intervals. Such calibrations are at least always required, when a new diaphragm is used. Normally, the life of the diaphragms is limited. Though they are in principle the same, there are deviations from diaphragm to diaphragm, which can be taken into consideration by a calibration. Further, such diaphragms do in many cases turn out to have an ageing behaviour, meaning that their permeability to the species changes over the time. Also for this reason periodical calibrations are required, to determine a "transition factor" of the diaphragm. This transition factor permits a derivation of the actual quantity or concentration of the species in the medium to be analysed on the basis of the load of species in the carrier fluid.

Such calibrations can be carried through in the laboratory without problems, as the corresponding measurements can be made in a controlled environment. As, however, application on site of analysis systems is gaining importance, for instance swimming in settling tanks in sewage disposal plant or in outfall ditches, and the recovery for calibration purposes is too expensive, it has been endeavoured to find solutions for carrying through calibrations on site, i.e. in the installation in question.

In an analysis system known from DE 44 24 494 A1, calibration is thus made in that two different carrier fluids are led past the diaphragm, which carrier fluids differ from each other with respect to the concentration of the species to be detected. The starting concentration in both fluids is known. The concentration after passing the diaphragm can be measured. This gives sufficient information to determine the penetration behaviour or the transition factor, which can be called "efficiency". In subsequent measurements this efficiency can be used to conclude or calculate the concentration of the species in the medium to be analysed on the basis of the load of species in the carrier fluid.

However, with the known system it is necessary to have two different carrier fluids. Thus, space must be provided for the corresponding reservoirs and for the corresponding pump or any other sort of flow controlling device.

The task of the invention is to reduce the constructional expenses connected with the calibration.

With a method as mentioned in the introduction, this task is solved in that, in a calibration step, the carrier fluid is stopped on the inside of the diaphragm for a predetermined sojourn time, after which the load of the species in the carrier fluid is determined, in a further calibration step the carrier fluid is led past the diaphragm at a speed also used for measurements and the load of the species in the carrier fluid is determined, and the penetration behaviour of the diaphragm is determined on the basis of both load values.

When the carrier fluid remains inside the diaphragm for a long time, a balancing of the concentrations of species on both sides of the diaphragm will occur, meaning that the concentration of species in the carrier fluid has exactly the same value as the concentration of species in the medium to be analysed. For this purpose, the fluid can be stopped on or led very slowly past the inside of the diaphragm. However, normally, the concentration balancing occurs according to an e-function or a similar function, and therefore there will still be concentration differences on both sides of the diaphragm after a certain time. For measuring technical purposes, however, they are so small that they can be disregarded. Thus, at this calibration step the actual concentration of species in the medium to be analysed is determined. In the other calibration step the carrier fluid is now led past the diaphragm in the way also used for the following measurements. The sojourn time of the carrier fluid on the inside of the diaphragm is then shorter, causing that ordinarily only smaller amounts of ions, molecules or similar particles of the species can penetrate the diaphragm into the carrier fluid. This will thus result in a lower concentration or loading of species in the carrier fluid. Now, e.g., the relation between the two loads or concentrations can be used to calculate the transition factor or the efficiency of the diaphragm. This transition factor can then be used for further measurements to calculate the concentration of species in the medium to be analysed on the basis of the determined load or concentration of species in the carrier fluid.

This procedure gives the advantage that an additional carrier fluid with a different concentration of the species must not be available in the system. An additional pump or an additional valve can also be saved. Thus, also a further possibility of errors is eliminated, which could occur in previous systems in that both pumps did not have the same discharge capacity. Until now, the consequence of this was that the costs for the pump were relatively high. It has turned out that a further advantage of the new calibration is that "intermediary flushing" is no longer necessary. On the contrary, only one single carrier fluid is required, which is the same for all calibration steps. After the last calibration step, measurements can be made immediately, as the correct fluid is already available in the flow path past the diaphragm to the detector.

Preferably, the carrier fluid is free of the species before being led past the diaphragm. Thus, there will be no zero-point displacement. An initial concentration of species in the carrier fluid must no longer be taken into consideration. On the contrary, the whole load of species in the carrier fluid originates from the penetration of species through the diaphragm.

Preferably, water is used as carrier fluid. In many cases water with the required purity will already be available. It is chemically neutral, thus additional security or protection measures are not required.

Advantageously, the flow path for the carrier fluid behind the diaphragm is interrupted for the duration of the sojourn time. This secures that the only way for the carrier fluid to have influence goes through the diaphragm. A mixing of the carrier fluid on the inside of the diaphragm and other fluids, which might be loaded with the species to be detected or other species, can thus not take place. This facilitates the following evaluation.

Preferably, a calibration of the following components of the system is made during the sojourn time. In many cases it is not only necessary to calibrate the diaphragm, i.e. establish its penetration or transition behaviour, or efficiency, respectively, but also to calibrate further components, as for instance the detector. For this purpose, a fluid with a known concentration of the species can be led past the detector, after which the output signal emitted by the detector is calibrated to the known concentration. To get more than one value, normally a series of carrier fluids with different concentrations are led to the detector for this calibration. In many cases, the concentration is determined on the basis of a colour reaction, meaning that reagents must be added, the reactions of which cause the colour change. This takes a certain time. Advantageously, this time can be used for the calibration of the diaphragm. Thus the total calibration time of the system will be short.

Advantageously, the calibration step, by which the carrier fluid remains on the inside of the diaphragm, takes place before the further calibration step. Thus measuring can start immediately after finishing the calibration. In this connection it is taken for granted that the concentration of species in the medium to be analysed will not change in the short time between the two calibration steps. Often a change will occur slowly over a long period of time.

Advantageously, the sojourn time is at least 5 minutes. After this relatively long period of time the required probability of the balancing of the species concentration on both sides of the diaphragm will be ensured. In many cases, however, shorter periods will do. The required time can be evaluated in that the concentration increase, occurring in accordance with an e-function, is determined, after which calculations are made to establish how long it will take to reach the desired maximum concentration.

In an analysis system as described in the introduction, the task is solved in that a blocking device is arranged on the outlet side of the flow path. With this blocking device it can be provided that the carrier fluid is kept on the inside of the diaphragm, so that influences from further sections of the flow path are eliminated. Thus, the influence of the carrier fluid can only take place through the diaphragm. The rather unusual measure of arranging a blocking device in the flow path after the diaphragm, e.g. a closing valve, facilitates the calibration considerably.

Advantageously, a blocking device is also arranged on the inlet side. This prevents the connection between the space on the inside of the diaphragm and the reservoir for the carrier fluid. Thus, no species can escape from this space and, e.g., reach the reservoir for the carrier fluid. On one hand this improves the recent calibration, on the other hand, however, also reduces the risk of faulty measurement results at future measurements.

In the following the invention is described on the basis of a preferred embodiment in connection with the drawing. The only FIGURE shows:

FIGURE: a schematic view of an analysing system.

An analysing system 1 has a diaphragm 2, the outside of which is immersed into a fluid 3 to be analysed. By this the diaphragm 2 covers a window in a schematically shown housing 4.

On the inside of the diaphragm 2, i.e. the side turned towards the inside of the housing 4, a flow path 5 is provided, which here is shown schematically by means of a line. The flow path 5 has an inlet 6, connected with a reservoir 8 via a pump 7, which reservoir 8 contains a carrier fluid 9. Here the carrier fluid 9 is water. However, also a different carrier fluid can be used, by which it is preferred that it contains nothing of the species to be detected. The section of the flow path 5 is known.

The flow path 5 has an outlet 13 connected with a detector 15 via a reaction channel 14. The reaction channel 14 is connected with reservoirs 22 to 27 via pumps 16 to 21, which reservoirs contain different fluids 28 to 33, e.g. water or reagents. Especially, the reservoir 22, which is connected with the reaction channel 14 close to the outlet 13 of the flow path 5, contains water for the cleaning of the reaction channel.

At the inlet 6 of the flow path 5 a shut-off valve 10 is arranged, which can interrupt the connection between the flow path 5 and the reservoir 8 with the carrier fluid 9. At the outlet of the flow path 13 a further shut-off valve 11 is provided, which interrupts a connection between the flow path 5 and the reaction channel 14. Thus a closed volume can be produced in the flow path 5, which volume is in connection with the inside of the diaphragm 2.

The pumps 7, 16 to 21, the shut-off valves 10, 11 and the detector 15 are connected with a control unit 34. The control unit 34 can control each pump 7, 16 to 21, individually. The volumetric delivery of the pumps 7, 16 to 21 can be dosed relatively exactly. With the corresponding control by the control unit 34, the quantity $Q_a$ of the fluid quantities supplied by the pumps 7, 16 to 21, will be available for the control unit 34. Thus information about the fluid quantity, transported through the flow path, is also available. Of course gaseous fluids can be used instead of fluids.

The shut-off valves 10, 11 are also in connection with the control unit 34, and can be opened and closed by it.

For measurements the carrier fluid 9 is led through the flow path 5 along the diaphragm 2 by means of the pump 7. Thus the species to be determined reaches through the diaphragm 2 into the carrier fluid 9 by diffusion or other transition processes. The initial concentration C of the carrier fluid 9 is known, and here it has the value zero.

In the reaction channel 14 the carrier fluid which is now available with a different concentration is supplied with reagents, e.g. causing a sedimentation or a colour change reaction, which can be registered by the detector 15, which may be constructed as a photo detector. The control unit 34 can convert the output signal of the detector 15 to a concentration value C*. For this the following equation applies:

$$\ln[1-(C^*-C)/(C_d-C)]=-k_0^*A/Q_a \quad (1)$$

by which

C=the concentration in the carrier fluid before passing the diaphragm

C*=the concentration in the carrier fluid after passing the diaphragm $C_d$=the (unknown) concentration in the fluid to be analysed $k_0$=a mass transition coefficient A=the effective surface of the diaphragm $Q_a$=the flow volume per time unit along the diaphragm From this the control unit 34 can determine the concentration $C_d$ of species in the fluid 3 to be analysed.

However, it is a condition here that the diaphragm qualities, which are mainly contained in the product $k_0 \times A$, are known. These "transition qualities" of the diaphragm are different from diaphragm to diaphragm, so that at least after each diaphragm replacement a calibration is required. However, due to influences from the environment, such as growth of algae, the transition qualities can also change during the operation time of a diaphragm. Thus it is in many cases also necessary to carry through calibrations from time to time.

To carry through a calibration, the reaction channel 14 is first cleaned with the water 28 in the reservoir 22. During this process a nullification of the detector 15 can be made at the same time. If so, a fluid from one of the other reservoirs 23 to 27 can be led to the detector, which fluid produces a measuring signal here, which can be used for the calibration of the detector 15. In this way the detector can be calibrated over a wider measuring range. Either a number of standard solutions, e.g. 0.2 and 5 PPM, are led to the detector and measured there, which solutions are already contained in the two reservoirs 23, 27. Or these standard solutions are produced through mixing of a standard solution with a higher concentration with water from the reservoir 22. Normally, the calibration of the detector 15 takes several minutes. In many cases a large share of the required time is used to finish reactions, in which for instance a colour change must take place to enable the reading of the species in the detector.

Before the calibration of the detector 15, or as first calibration step of the detector 15, water 9 is pumped from the reservoir 8 by means of the pump 7 through the flow path 5 and possibly through the reaction channel 14 to the detector 15. At any rate, it must be provided that the flow path 5 is completely filled with water. When this is the case, the steering device 34 closes the shut-off valves 10 and 11. Then the calibration of the detector 15 can take place, which does, as stated above, take a certain time, for example 5, 6 minutes or more. During this period the water in the flow path 5 absorbs species, e.g. phosphate, nitrate or the like, from the fluid 3 to be analysed. Thus, after a certain time, there will be a balance of the species on both sides of the diaphragm 2, i.e. the concentration of the species in the water in the flow path 5 is exactly as high as the concentration of the species in the fluid 3 to be analysed. As both shut-off valves 10 and 11 are closed, the species penetrating the diaphragm 2 can only concentrate in the volume of the water contained in the flow path 5.

When the detector 15 has been calibrated, and the reaction channel has been cleaned with water, if necessary, the water originating from the flow path 5 can be led through the detector 15. Thus the detector 15 can determine the concentration of species in this volume of the water as carrier fluid. This concentration corresponds to the concentration of the species in the fluid 3 to be analysed.

In a further calibration step, water 9 from the reservoir 8 is again pumped through the flow path 5 by means of the pump 7, this time with a speed or a volume flow corresponding to that of a normal measurement. As the sojourn time on the inside of the diaphragm is then shorter, the load of this carrier fluid with the species will be lower, so that the detector 15 finds a lower concentration of the species in the carrier fluid. When it is now assumed that the concentration in the fluid 3 to be analysed has not changed during the short interval between the two calibration steps, the equation (1) can be used to calculate the product $K_0 \times A$. This product then also applies for the following measurements. By means of this product the concentration of species in the fluid 3 to be analysed can be calculated on the basis also on the basis of later measurements, namely by using the value $C^*$.

The advantage of this procedure is that before the flow path 5 only one single reservoir 8 and one single pump 7 are required. As for the calibration only one single carrier fluid 9, in this case water, is used, and this carrier fluid is also required for the following measurements, the measurement can be made immediately after the calibration, without having to carry through a cleaning of the reaction channel 14. Thus carrier fluid 9 and possibly also additional reagents are saved.

What is claimed is:

1. Method for calibration of an analysis system having a diaphragm, an outside of which is immersed into a medium to be analysed, and on the inside of which a carrier fluid for the admission of a species penetrating the diaphragm is flowing, the method comprising the steps of stopping the carrier fluid on the inside of the diaphragm for a predetermined sojourn time, determining the load of the species in the carrier fluid, leading the carrier fluid past the diaphragm at a speed also used for measurements, again determining the load of the species in the carrier fluid, and determining the penetration behaviour of the diaphragm from both determined loads.

2. Method according to claim 1, in which the carrier fluid is free of the species before being led past the diaphragm.

3. Method according to claim 1, in which water is used as the carrier fluid.

4. Method according to claim 1, in which the flow path for the carrier fluid to the diaphragm is interrupted for the duration of the sojourn time.

5. Method according to claim 1, in which a calibration of the following components of the system is made during the sojourn time.

6. Method according to claim 1, in which the step of stopping the carrier fluid on the inside of the diaphragm takes place before the step of leading the carrier fluid past the diaphragm.

7. Method according to claim 1, in which the sojourn time is at least 5 minutes.

8. Analysis system with a diaphragm, the diaphragm having an outside which is immersed into a medium to be analysed, a flow path located on the inside of the diaphragm, the flow path having an inlet side connected to a reservoir of a carrier fluid and the outlet side connected to a detector, the analysis system further incorporating a control unit, a pump for pumping the carrier fluid and a blocking device which is located on the outlet side of the flow path, the control unit, in a first step, blocking the blocking device for creating a first sojourn time of the carrier on the inside of the diaphragm and, in a next step, the control unit controlling either the blocking device or the volumetric delivery of the pump for creating a second sojourn time which is shorter than the first time.

* * * * *